United States Patent [19]

Blevins, II et al.

[11] Patent Number: 5,110,970

[45] Date of Patent: May 5, 1992

[54] PROCESS FOR THE MANUFACTURE OF CERTAIN NEW SILICONE POLYETHER COPOLYMERS FOR POLYURETHAN FOAM MANUFACTURE

[75] Inventors: Charles H. Blevins, II, San Jose, Calif.; Paul L. Matlock, Ossining; Gerald J. Murphy, Hopewell Junction, both of N.Y.

[73] Assignee: Union Carbide Chemicals & Plastics Technology Corporation, Danbury, Conn.

[21] Appl. No.: 677,148

[22] Filed: Mar. 29, 1991

[51] Int. Cl.$^5$ .............................. C07F 7/08; C07F 7/18
[52] U.S. Cl. ........................................ 556/445; 556/442
[58] Field of Search .................................. 556/445, 442

[56] References Cited

U.S. PATENT DOCUMENTS

| | | | |
|---|---|---|---|
| 2,834,748 | 5/1958 | Bailey et al. | 260/42 |
| 2,846,458 | 8/1958 | Haluska | 260/448.2 |
| 2,917,480 | 12/1959 | Bailey et al. | 260/42 |
| 3,194,773 | 7/1965 | Hostettler | 260/2.5 |
| 3,470,226 | 9/1969 | Plumb et al. | 260/448.8 |
| 3,503,943 | 3/1970 | Kresge et al. | 260/80.78 |
| 3,505,377 | 4/1970 | Morehouse et al. | 260/448.2 |
| 3,573,334 | 3/1971 | Wheeler | 260/448.2 |
| 3,703,489 | 11/1972 | Morehouse | 260/2.5 AH |
| 3,755,399 | 8/1973 | Nitzsche et al. | 260/448.8 R |
| 3,798,253 | 3/1974 | Rick et al. | 260/448.2 B |
| 3,957,843 | 5/1976 | Bennett | 260/448.2 B |
| 4,059,605 | 11/1977 | Bennett | 260/448.2 B |
| 4,090,987 | 5/1978 | Koerner et al. | 260/2.5 AH |
| 4,150,048 | 4/1979 | Schilling, Jr. et al. | 260/448.2 B |
| 4,160,775 | 7/1979 | Schilling, Jr. | 260/448.2 E |
| 4,424,328 | 1/1984 | Ellis | 526/279 |
| 4,514,315 | 4/1985 | Matulewicz et al. | 252/75 |
| 4,962,218 | 10/1990 | Blevins et al. | 556/445 |
| 5,001,248 | 3/1991 | Grabowski | 556/445 X |

FOREIGN PATENT DOCUMENTS 892136  3/1962  United Kingdom .

Primary Examiner—Paul F. Shaver
Attorney, Agent, or Firm—Bonnie L. Deppenbrock

[57] ABSTRACT

This invention relates to silicone surfactants, and more particularly, to synthesis of siloxane-polyether surfactants having polyether backbones.

6 Claims, 1 Drawing Sheet

PROCESS FOR THE MANUFACTURE OF CERTAIN NEW SILICONE POLYETHER COPOLYMERS FOR POLYURETHAN FOAM MANUFACTURE

BACKGROUND OF THE INVENTION

U.S. Pat. No. 4,962,218 discloses silicone-polyether copolymer surfactants for polyurethane foam manufacture, having polyether backbones with lateral and/or terminal siloxane pendants. Such materials are referred to as "inverted surfactants," because conventional silicone-polyether surfactants having siloxane backbones and polyether pendant groups. They were synthesized by hydrosilating a polyether bearing multiple olefinic pendants with a silicone precursor of the desired siloxane pendants, having the desired size and molecular weight. To prevent crosslinking reactions, this silicone intermediate had to be highly pure and could possess only one silanic hydrogen per molecule. Since normal, commercially relevant silicone production schemes involve an equilibration process, methods such as careful distillation of an equilibrated fluid (very labor intensive and inefficient) or non-equilibration routes such as those employed in U.S. Pat. No. 4,962,218 (also very labor intensive, using non-trivial techniques and air and moisture sensitive reactants) needed to be invoked to prepare the required monofunctional silicone Si-H fluid intermediates. As such syntheses of the required silicone intermediates involved non-trivial synthetic methods not currently commercially practiced, and/or required purification by laborious and expensive techniques, the resulting surfactants were commercially disadvantaged.

In addition, hydrosilations with certain types of silicone intermediates were inefficient, particularly the reaction employing the sterically bulky tris-(trimethylsiloxy)silane (hereinafter abbreviated $M_3T'$ in accordance with accepted practice, M standing for $Me_3SiO_{1/2}$ where Me represents a methyl group, and T' standing for $HSiO_{3/2}$). Conversions of the polyether's olefinic pendants into silicone pendants were typically less than 45% for these reactions.

It is therefore desirable to have an improved synthetic route to these surfactants. Such a synthesis is the subject of the present application.

The first disclosure of polysiloxane polyoxyalkylene copolymers appears in U.S. Pat. No. 2,834,748 of Bailey, et al. These compositions were of the hydrolyzable type, having siloxane backbones and polyether pendant groups attached to the siloxane via Si-O-C linkages. Subsequently, the first disclosure of non-hydrolyzable polysiloxane polyoxyalkylene copolymers, in which the polyether pendants are attached to the siloxane backbone via C-O-C linkages, appears in U.S. Pat. No. 2,846,458 of Haluska.

The first application of polysiloxane polyoxyalkylene copolymers for the stabilization of urethane foam appeared in British Patent No. 892,136 of Hostettler. These copolymers were of the hydrolyzable type. The application of non-hydrolyzable copolymers to urethane foam stabilization soon followed.

In U.S. Pat. No. 3,573,334 of Wheeler, a vinyl siloxane cohydrolyzate was free radically grafted onto a nominally 2800 g/mole polyether (50% by weight oxyethylene and 50% by weight oxypropylene units). See Example II of the patent. The use of a vinyl siloxane cohydrolyzate rather than a pure mono(vinyl)siloxane ensured that true inverted copolymer structures would not be obtained. In fact, Wheeler did not disclose preparation of such a structure in this patent.

One example is known in which a polyether prepared by the coalkoxylation of propylene oxide and allylglycidylether (i.e. a PPO rubber) was grafted by a silane. See U.S. Pat. No. 3,305,943 to ESSO Research and Engineering. The resulting compositions are rubbers which would be unacceptable for the presently-contemplated end uses.

In the abstract of Japanese Patent 54/36397 to Kanegafuchi Chemical Industry Co., Ltd., it is disclosed that an alkoxysilane was grafted via hydrosilation to an allylglycidylether modified polyester (1,2-butylene oxide-phthalic anhydridepolyethylene glycol copolymer). These ether-ester block copolymeric compositions were used as coating and room temperature curable compositions.

U.S. Pat. No. 4,424,328 deals with modified methacrylate monomers useful in manufacture of polymers for contact lenses. It discloses addition of a hydrolyzable silane with one silanic hydrogen to a monomeric olefin-modified methacrylate, to yield a hydrolyzable silane-modified methacrylate which is next cohydrolyzed with silane monomers to yield a silicone-modified methacrylate monomer. Subsequent free-radical polymerization of this material yields a silicon-pendant PMMA plastic. This concept of polymerizing a silicone-modified monomer is inappropriate to prepare the inverted surfactants of interest in the present case since the necessary hydrolyzable silane-pendant epoxide monomer would undergo hydrolysis during the base-catalyzed alkoxylation reaction which produces the polyether.

SUMMARY OF THE INVENTION

This invention relates to a new process for synthesizing silicone-polyether copolymer surfactants having polyether backbones with lateral and/or terminal siloxane pendants ("inverted surfactants"), which surfactants are useful as stabilizers for polyurethane foam.

The invention is an improved method for preparing a polyether-siloxane copolymer having a polyether backbone, and comprises the following steps:

a) providing a polyether possessing olefinically-unsaturated pendant groups;

b) reacting this polyether with a silane having an Si-H group and at least one hydrolyzable functional group, to form an intermediate in which olefinically-unsaturated groups of the polyether have been converted into silane-containing groups; and c) reacting this intermediate polyether-silane under hydrolytic conditions with a second silane, which has at least one hydrolyzable functional group, or with a siloxane possessing 1-3 hydrolyzable groups, to form a polyether-siloxane copolymer in which silane-containing groups of the intermediate have been converted into siloxane-containing groups.

This process has the following advantages, relative to the method of preparing such materials disclosed in U.S. Pat. No. 4,962,218:

it uses relatively inexpensive commercially available hydrolyzable silanes as reactants in the hydrosilation step with the multiply-olefinically pendant polyethers, instead of the hydrido-silicones employed in the '218 process;

it affords generally higher yields and higher degrees of conversion of olefinic pendant groups to siloxane pendant groups, relative to the '218 process;

it is more facile than the previously disclosed process.

it permits preparation of inverted surfactants containing bulky siloxane pendant groups such as the $M_3T'$ group with considerably higher yields and higher conversions of pendant olefins to pendant silicones relative to the state-of-the-art yields and conversions;

as a consequence of the nature of the starting materials for preparation of these copolymers, the final product mixtures contain essentially no residual unreacted polyether and are therefore essentially all copolymer, with little or no ineffective homopolymers being present;

it produces inverted surfactants having higher purity and more narrow molecular weight distributions than those of the '218 process; and intermediates and products employed in this process are more easily purified than those of the previous process.

In sum, the process of the invention overcomes the synthetic and purification disadvantages of the state-of-the-art process, which consequently makes it more commercially viable than the prior art process from both process and cost standpoints.

DESCRIPTION OF THE DRAWING

The invention will be more completely understood from a consideration of the following detailed description, taken in conjunction with the drawing, in which.

DETAILED DESCRIPTION OF THE INVENTION

Figure 1:
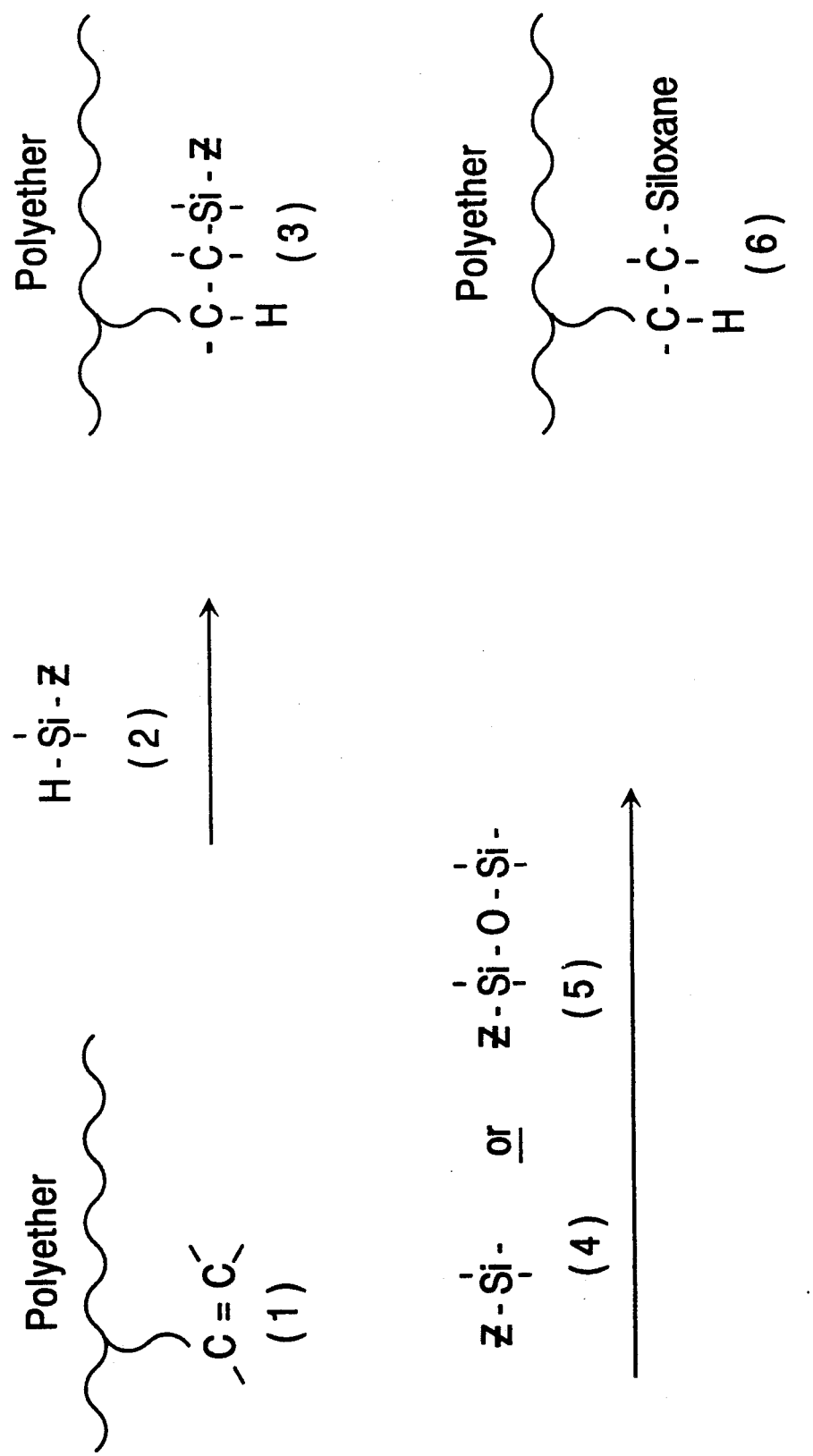
FIG. 1 is a generalized schematic illustrating the process of the invention.

In the process of the invention, the starting material (1) is a polyether possessing multiple olefinically-unsaturated pendant groups. As employed in this application, the expression "pendant groups" means groups which are attached to the polyether chain along its length or at its ends. The polyether may be linear or branched and must have at least two olefinically-unsaturated pendant functional groups in its pre-reacted state.

Such unsaturated polyether materials are prepared in the manner known to the art, by copolymerization of mixtures of alkylene oxides such as ethylene oxide and propylene oxide and unsaturated epoxides such as allyl-glycidylether, as discussed in U.S. Pat. No. 4,962,218 from column 5 line 1, to column 6 line 45, as shown in application Ser. No. 07/268,187 from page 10 line 21 to page 12 line 10, which text is hereby incorporated by reference.

Starting polyether (1) is reacted with a silane (2) having an Si-H group and at least one hydrolyzable functional group Z, to form an intermediate polyether-silane (3) in which olefinically-unsaturated groups of the original polyether have been converted into silane-containing groups.

This reaction between an olefinic functional group and a silane bearing an Si-H bond is termed hydrosilation, and is carried out by heating the reactants in the presence of a platinum-containing catalyst, in the manner known to the art. Desired amounts of polyether (1) containing olefinic pendants are combined with silane (2), generally under an inert atmosphere such as nitrogen and in the presence of a solvent such as toluene to facilitate heat dissipation, and a catalytic amount of a solution of a hydrosilation catalyst such as chloroplatinic acid is added. The reaction flask is warmed to initiate the reaction, and after an initial exotherm, the mixture is heated to about 90° C-110° C. and held at this temperature for about 0.1-2 hours. The flask contents are then neutralized, and the heating is generally continued for a further 1-2 hour period of time, then filtered, and the product is isolated by removing volatile materials. The conditions for carrying out this reaction are illustrated in Examples I-XVII of U.S. Pat. No. 4,962,218.

Any silane (2) having an Si-H bond and at least one reactive hydrolyzable functional group may be employed in the hydrosilation step, provided that the silane portion of the resultant polyether-silane (3) can be reacted, as described below, with a silane or siloxane having a reactive hydrolyzable functional group. Silane (2) is selected in consideration of silane (4) or siloxane (5) discussed below, so that the silane (2) employed leads ultimately to a product polyether-siloxane having the desired properties.

Preferred silanes (2) for use in the hydrosilation reaction have the general formula $HSiZ_zR_{3-z}$ wherein R is an alkyl group of 1-3 carbon atoms; Z is halogen, —OR, or —OC(O)R; and z is an integer of 1-3. Most preferred silanes are those in which R is methyl, Z is Cl or OR, and z is 1 or 2.

Examples of such silanes are trichlorosilane, triethoxysilane, trimethoxysilane, dichloromethylsilane, diethoxymethylsilane, diacetoxymethylsilane, and chlorodimethylsilane.

Silanes (2) having an Si-H group and at least one hydrolyzable functional group Z are commercially available.

Intermediate polyether-silane (3) is isolated by stripping the more volatile materials, and used without further purification.

Intermediate polyether-silane (3) is next reacted with a second silane (4), which has at least one hydrolyzable functional group, or with a siloxane (5) possessing 1-3 hydrolyzable groups, to form a polyether-siloxane copolymer (6) in which silane-containing groups of the intermediate have been converted into siloxane-containing groups. Typically, this reaction is carried out under hydrolytic conditions, in the presence of alcohol and water.

Any silane (4) or siloxane (5) may be employed in the reaction with polyether-silane (3) provided that it possesses a suitable hydrolyzable functional group, and will react with polyethersilane (3) to yield the desired product.

Preferred silanes (4) for use in the process have the general formula $SiZ_{z'}R_{4-z'}$ wherein R and Z are as defined above, and z' is an integer of 1-2. Most preferably, z' is 1. Examples of such materials are dichlorodimethylsilane, chlorotrimethylsilane, trimethylacetoxysilane, trimethylethoxysilane, and dimethyldiethoxysilane.

Preferred siloxanes (5) for use in the process possess 2-8 silicon atoms, and are comprised of units having the general formula

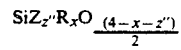

wherein R and Z are as defined above, z" is an integer of 0-1, x is an integer of 1-3, and x+z" is 2-3. Most preferably, x is 2-3.

Examples of such materials are
$Cl(Me)_2SiO\{Si(Me)_2O\}_nSi(Me)_2Cl$,
$(Me)_3SiOSi(Me)_2OAc$, and
$((Me)_3SiO)_2(Me)SiOEt$,
wherein Me stands for a methyl group, Et stands for an ethyl group, OAc stands for an acetoxy group, and n is 0 or a number of 1 to 6.

When the number of hydrolyzable groups Z in silane (2) is three, the number of hydrolyzable groups Z in silane (4) or siloxane (5) is one. When the number of hydrolyzable groups Z in silane (2) is one or two, the number of hydrolyzable groups Z in silane (4) or siloxane (5) is one or two. Further, those skilled in the art will recognize that using alkoxy instead of a halogen such as chlorine as the hydrolyzable groups Z in the silanes and siloxanes employed as reagents in the process eliminates the need to deal with HCl as a by-product.

The silanes (4) which have at least one hydrolyzable functional group, as well as the siloxanes (5) possessing 1-3 hydrolyzable groups, are commercially available or easily prepared.

In the final polyether-siloxane block copolymer product (6) the siloxane blocks may be linear, branched or cyclic, depending on the reagents employed in their synthesis.

In Table 1 below are illustrated a number of siloxane groups attached as pendants to polyether chains, and the reagents from which they may be synthesized according to the process of the invention. In the table, the letter Z stands for a halogen, an alkoxy group OR wherein R contains 1-3 carbon atoms, or an acyloxy group OC(O)R wherein R contains 1-3 carbon atoms. Examples of these functionalities are Cl, methoxy or ethoxy, and acetoxy, respectively. It is to be understood that the polyether possesses multiple olefinically-unsaturated groups, only one of which is illustrated.

TABLE 1

Examples of products for the reaction:

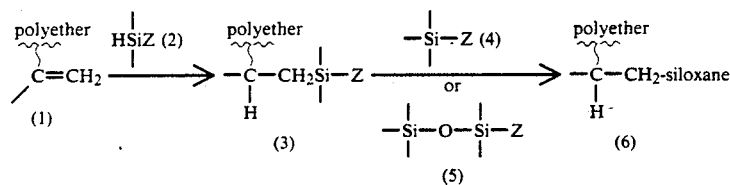

| Silane (2) | Silane (4) or Siloxane (5) | Product |
|---|---|---|
| $HSiZ_3$ | $Me_3SiZ$ | polyether-C(H)-CH$_2$-Si(OSiMe$_3$)$_3$ |
| $HSiZ_2Me$ | $Me_3SiZ$ | polyether-C(H)-CH$_2$-Si(OSiMe$_3$)$_2$Me |
| $HSiZMe_2$ | $Me_3SiZ$ | polyether-C(H)-CH$_2$-Si(Me)$_2$-OSiMe$_3$ |
| $HSiZMe_2$ | $Me_3SiZ$ + n eq. of $Me_2SiZ_2$ | polyether-C(H)-CH$_2$Si(Me)$_2$-(OSi(Me)$_2$)$_n$-OSiMe$_3$ |
| $HSiZ_2Me$ | n eq. of $Me_2SiZ_2$ | polyether-C(H)-CH$_2$Si(Me)-[OSi(Me)$_2$-O]$_n$ |

TABLE 1-continued

Examples of products for the reaction:

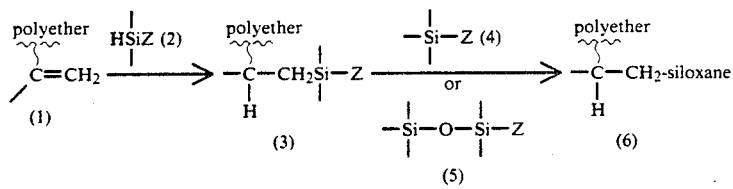

| Silane (2) | Silane (4) or Siloxane (5) | Product |
|---|---|---|
| HSiZ$_2$Me | Z—Si(Me)(Me)—O—[Si(Me)(Me)—O]$_n$—Si(Me)(Me)—Z | polyether-C(H)-CH$_2$-Si(Me) cage structure with O-Si(Me)$_2$, O-Si(Me)$_2$, OSi(Me)(Me) groups |
| HSiZ$_2$Me | Me$_3$SiOSi(Me)(Me)—Z | polyether-C(H)-CH$_2$-Si(Me)-O-Si(Me)(Me)-OSiMe$_3$ with O-Si(Me)(Me)-OSiMe$_3$ branch |
| HSiZ$_2$Me | Me$_3$SiO—Si(Me)(OSiMe$_3$)—Z | polyether-C(H)-CH$_2$-Si(Me)-O-Si(Me)(OSiMe$_3$)-OSiMe$_3$ with Me$_3$SiO-Si(Me)(OSiMe$_3$) branch | an alternative route to the desired polyether-siloxane copolymers involves the use of alkoxysilane grafted intermediates such as those disclosed in U.S. Pat. No. 4,514,315 (wherein several examples describe the grafting of vinylalkoxysilanes and allylalkoxysilanes to polyethers) and in U.S. Pat. No. 3,503,943 (wherein several examples describe the grafting of chlorosilanes, alkylchlorosilanes, alkoxysilanes, alkylalkoxysilanes, acyloxysilanes and acyloxyalkylsilanes to polyethers). From these intermediates, then, one can prepare the silicone analogs by use of reactive silanes or siloxanes as described above.

EXAMPLES

Example I (process of U.S. Pat. No. 4,962,218)

Into a clean, dry 250 mL three neck round bottom flask was placed 32.58 grams of (Me$_3$SiO)$_3$SiH (M$_3$T', prepared via a cohydrolysis of Cl$_3$SiH and Me$_3$SiCl with isopropanol and water, followed by careful vacuum distillation), 27.46 grams of a polyether (16.4% allyl: 3.52% OH (diol); made by polymerization of 48% allylglycidylether, 24% ethylene oxide and 28% propylene oxide by weight), and 26.01 grams of toluene. These charges represent a 1:1 stoichiometry of allyl to SiH and 30% dilution in toluene. The flask was equipped with a mechanical stirrer, heating mantle, Dean-Stark trap, nitrogen sparge tube and outlet, thermometer and thermowatch, and Friedrich's condenser.

The flask was heated to 85° C. and a light nitrogen sparge was instituted. A small amount of clear (dry) toluene was collected, ensuring dehydrated starting materials. The flask temperature was increased to 108° C., at which time catalysis was effected by the addition of 0.25 mL (29 ppm Pt) of chloroplatinic acid/ethanol solution (10mg Pt/mL). An exotherm of 4° C. was observed to take the flask to 112° C. over the course of 3 minutes. Recatalysis with 0.1 mL (12 ppm) of the catalyst solution yielded no further exotherm. Flask contents turned brown after 20 minutes at 110° C.. The flask was held at 110° C. for another 95 minutes. The solution was then neutralized with 5.5 grams moist NaHCO$_3$ and was held at 100° C. for 120 minutes. The solution was then filtered through a 3-4 micron filter pad under 40 psi nitrogen to yield a clear brown toluene solution. Toluene was removed via a nitrogen sparge-assisted strip at 100° C.. 25.77 grams of a clear, brown product was collected (44% yield). GC of the stripped distillated revealed considerable recovered, unreacted M$_3$T'.

13$_C$ nmr analysis revealed roughly 40% conversion of the allyl groups to the hydrosilated silicone pendant. The remainder were observed as the isomerized propenyl functionalities. The steric bulk of the M$_3$T' silicone was implicated in the low conversion and this and similar hydrosilation reactions.

Previous work had demonstrated the utility of this and other M₃T' pendant inverted surfactants for the stabilization of rigid polyurethane foam.

Example II (New Process, first stage)

This example describes the synthesis of the hydrolyzable silane pendant polyether which will be used in Example III to prepare the silicone pendant polyether.

Into a clean, dry 250 mL three neck round bottom flask was placed 46.16 grams of a polyether (4.2% allyl; 0.45% OH (monol), prepared by polymerization of 13% allylglycidylether, 34% ethylene oxide, and 53% propylene oxide by weight), and 24.06 grams of toluene. The flask was equipped with a mechanical stirrer, heating mantle, Dean-Stark trap, nitrogen sparge tube and outlet, thermometer and thermowatch, and Friedrich s condenser. This was heated to 95° C., at which time a short nitrogen sparge-assisted strip revealed the contents to be dehydrated. The flask was cooled to 80° C. and 7.77 grams of HSi(OEt)₃ (Petrarch lot #44127) were added. This charge represents a 1:1 stoichiometry of allyl to SiH.

The reaction mixture was then catalyzed with 0.2 mL (26 ppm at Pt) of CPA/ethanol solution (10 mg Pt/mL) at 83° C.. After a 5 second induction period, a 10 degree exotherm was observed, taking the temperature to 93° C. over the course of two minutes. The flask was held at 90° C. for 10 minutes, after which the mixture was neutralized with 8.4 grams of NaHCO₃. The temperature of 90° C. was maintained for an additional 120 minutes. The contents of the flask were cooled to 33° C. and filtered through a 3-4 micron filter pad under 40 psi nitrogen. Toluene was then removed via a nitrogen sparge-assisted strip at 90° C.. 36.36 grams of a clear, pale yellow, viscous product was collect (67% yield).

Gravimetric analysis gave 2.1% Si compared to a theoretical 2.4%, for an 85% conversion of the allyl groups to silane groups.

Example III (New Process, second stage)

Into an ice-cooled 100 mL three neck round bottom flask, set up with a mechanical stirrer, dropping funnel, Friedrich's condenser, and nitrogen inlet/outlet, was placed 15.0 grams of the silane pendant polyether from Example II. Next, 2.4 grams of Me₃SiCl (100% molar excess) was added to the flask with stirring. Then isopropanol was added dropwise from the dropping funnel (starting at about 5° C.) at about 1 drop per second. Immediate gas evolution was observed (most likely HCl). A total of 30.17 grams of isopropanol was added. Next, 0.62 grams of water was added dropwise with about 3 mL of isopropanol. The flask was then warmed to room temperature with continued stirring. After 2.5 hours at room temperature, the volatiles (isopropanol, ethanol and water) were distilled off. 12.2 grams of a viscous liquid were collected (78% yield in this step and 52% yield overall).

29$_{Si}$ nmr revealed greater than 95% conversion of the silane to silicone units which represents a total conversion of at least 80% from the allyl pendants of the starting polyether to silicone pendants in the product. This is a dramatic improvement over the 40% conversion of allyl groups in the comparative example (I). The 52% yield from this process is also an improvement over the 44% yield of the previous process.

Other embodiments of the invention will be apparent to those skilled in the art from a consideration of this specification or practice of the invention as disclosed herein. It is intended that the specification and examples be considered as illustrative, with the true scope and spirit of the invention being limited only by the following claims.

We claim:

1. A method for preparing a polyether-siloxane copolymer having a polyether backbone, comprising the following steps:
    a) providing a polyether possessing olefinically-unsaturated pendant groups;
    b) reacting said polyether with a silane having an Si-H group and at least one hydrolyzable functional group, to form an intermediate polyether-silane; and
    c) reacting said intermediate polyether-silane under hydrolytic conditions with a silane possessing at least one hydrolyzable functional group, or with a siloxane possessing 1-3 hydrolyzable groups, to form a polyether-siloxane copolymer.

2. The method of claim 1 wherein the olefinically-unsaturated pendant groups of said polyether are vinyl groups.

3. The method of claim 1 wherein in said step of reacting polyether with a silane having an Si-H group, said silane has the general formula HSiZ$_z$R$_{3-z}$ wherein R is an alkyl group of 1-3 carbon atoms; Z is halogen, —OR, or —OC(O)R; and z is an integer of 1-3.

4. The method of claim 1 wherein in said step of reacting said intermediate polyether-silane under hydrolytic conditions, said silane has the general formula SiZ$_{z'}$R$_{4-z'}$ wherein R is an alkyl group of 1-3 carbon atoms; Z is halogen, —OR, or —OC(O)R; and z' is an integer of 1-2.

5. The method of claim 1 wherein in said step of reacting said intermediate polyether-silane under hydrolytic conditions, said siloxane is comprised of units having the general formula

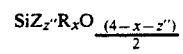

wherein R is an alkyl group of 1-3 carbon atoms; Z is halogen, —OR, or —OC(O)R; z" is an integer of 0-1, X is an integer of 1-3, and x+z" is 2-3.

6. A method for preparing a polyether-siloxane copolymer having a polyether backbone, comprising the steps of:
    a) providing a polyether possessing olefinically-unsaturated pendant groups;
    b) reacting said polyether with a silane of the formula HSiZ$_z$R$_{3-z}$ wherein
        R is an alkyl group of 1-3 carbon atoms,
        Z is halogen, —OR, or —OC(O)R, and
        z is an integer of 1-3,
    to form an intermediate in which olefinically-unsaturated groups of said polyether have been converted into silane-containing groups; and
    c) reacting said intermediate with one of:
        a silane of the formula SiZ$_{z'}$R$_{4-z'}$ wherein R and Z are as defined above, and
        z' is an integer of 1-2; and
        a siloxane possessing 1-3 groups Z and 2-8 silicon atoms, and comprising units of the formula $$SiZ_{z''}R_xO_{\frac{(4-x-z'')}{2}}$$

wherein

R and Z are as defined above, $z''$ is an integer of 0–1, x is an integer of 1–3, and $x+z''$ is 2–3;

to form a polyether-siloxane copolymer in which silane-containing groups of said intermediate have been converted into siloxane-containing groups.

* * * * *